US00RE39816E

(19) United States
(12) Reissued Patent
Stanton et al.

(10) Patent Number: US RE39,816 E
(45) Date of Reissued Patent: Sep. 4, 2007

(54) CONJUNCTIVE ANALYSIS OF BIOLOGICAL MARKER EXPRESSION FOR PREDICTING CARDIAC MORTALITY

(75) Inventors: Eric B. Stanton, Burlington (CA); George Jackowski, Kettleby (CA)

(73) Assignee: Nanogen Inc., San Diego, CA (US)

(21) Appl. No.: 11/117,772

(22) Filed: Apr. 29, 2005

Related U.S. Patent Documents

Reissue of:
(64) Patent No.: 6,461,828
Issued: Oct. 8, 2002
Appl. No.: 09/946,171
Filed: Sep. 4, 2001

(51) Int. Cl.
*G01N 33/543* (2006.01)

(52) U.S. Cl. ..... 435/7.92; 435/7.93; 435/7.94; 435/969; 435/970; 435/973; 435/975; 436/807; 436/808; 436/810; 436/514; 436/518; 436/528; 436/530; 422/60; 422/61

(58) Field of Classification Search ..... 435/7.92, 435/7.93, 7.94, 969, 970, 973, 975, 528, 435/530, 807, 808, 810; 436/514, 518
See application file for complete search history.

(56) References Cited

U.S. PATENT DOCUMENTS

| | | | |
|---|---|---|---|
| 5,290,678 | A | 3/1994 | Jackowski |
| 5,580,722 | A | 12/1996 | Foulkes et al. |
| 5,604,105 | A | 2/1997 | Jackowski |
| 5,747,274 | A | 5/1998 | Jackowski |
| 5,786,163 | A | 7/1998 | Hall |
| 5,795,725 | A | 8/1998 | Buechler et al. |
| 6,117,644 | A | 9/2000 | Debold |
| 6,156,521 | A | 12/2000 | Buechler et al. |
| 6,162,902 | A | 12/2000 | Mischak et al. |
| 6,174,686 | B1 | 1/2001 | Buechler et al. |
| 2003/0022235 | A1 | 1/2003 | Dahlen et al. |
| 2003/0109420 | A1 | 6/2003 | Valkirs et al. |
| 2004/0171064 | A1 | 9/2004 | Dahlen et al. |

FOREIGN PATENT DOCUMENTS

| | | | |
|---|---|---|---|
| WO | WO 91/09627 | A1 | 7/1991 |
| WO | WO 02/083913 | A1 | 10/2002 |
| WO | WO 03/020123 | A2 | 3/2003 |

OTHER PUBLICATIONS

Ishii, Junnichi et al., "Early Risk Stratification Using Cardiac Troponin T and Brain Natriuretic Peptide in Patients with Congestive Heart Failure." Supplement to *Circulation*, vol. 110, No. 18, Nov. 2, 1999; p. I.679 XP009005614, $72_{nd}$ Scientific Sessions of the American Heart Asso., Nov. 7–10, 1999.

Croal, B.L. et al., "Cardiac Troponin I and Brain Natriuretic Peptide as Markers of Doxorubicin Cardiotoxicity," *Clinical Chemistry*, vol. 47, No. S6, Jun. 2001 (2001–06); p. A149 XP001145792, $53_{rd}$ Annual Meeting of the AACC/CSCC, Chicago, Ill., Jul. 29–Aug. 2, 2001.

Langenbach, M.R., et al., "Das Atriale Natriuretische Peptid als Indikator einer Milden Postoperativen Kardialen Dysfunktion Nach Unkomplizierter Bypasschirurgie," *Zeitschrift Fuer Karkiologie*, vol. 89, No. 12, 2000, pp. 1133–1140; XP 002231029.

Li, D. et al, "Greater Frequency of Increased Cardiac Troponin T than Increased Cardiac Troponin I in Patients with Chronic Renal Failure," *Chemical Chemistry*, CLCHAU 42 (1) 114–115 (1996).

McCullough, P. et al., "Beyond Serum Creatinine: Defining the Patient with Renal Insufficiency and Why?" *Reviews in Cardiovascular Medicine*, vol. .4, Suppl 1 2003, S2–S6.

McCullough, P., et al., "B–type Natriuretic Peptide and Renal Function in the Diagnosis of Heart Failure: An Analysis From the Breathing Not Properly Multinational Study," *Am. J. of Kidney Diseases*, vol. 41, No. 3 (Mar.) 2003; pp. 571–579.

Ziesche, S., et al. "Interobserver Discordance in the Classification of Mechanisms of Death in Studies of Heart Failure," *J. of Cardiac Failure*, vol. 1, No. 2, Mar. 1995, pp. 127–132.

Nolan, J., et al., "Prospective Study of Heart Rate Variability and Mortality in Chronic Heart Failure," *Results of the UK Heart Failure Evaluation and Assessment of Risk Trial (UK–Heart)*, 1998 pp. 1510–1516.

Ishii, J., et al., "Prognostic Value of Combination of Cardiac Troponin T and B–Type Natriuretic Peptide after Initiation of Treatment in Patients with Chronic Heart Failure," *Clinical Chemistry*, 49:12, 2020–2026 (2003).

Ishii, J., et al., "Risk Stratification Using a Combination of Cardiac Troponin T and Brain Natriuretic Peptide in Patients Hospitalized for Worsening Chronic Heart Failure," *Amer. J. of Cardiology*, vol. 89, pp. 691–695, Mar. 15, 2002.

Ishii J., et al., "Plasma concentration of brain natriuretic peptide as a biochemical marker for the evaluation of right ventricular overload and mortality in chronic respiratory disease," *Clinica Chimica Acta*, 301 (2000) 19–30.

De Lemos et al., "The Prognostic Value of B–Type Natriuretic Peptide in Patients with Acute Coronary Syndromes," *The New England Journal of Medicine*, vol. 345, No. 14, Oct. 4, 2001.

Chen et al., "The natriuretic peptides in heart failure: Diagnostic and therapeutic potentials," *Proc. Assoc. Amer. Phys.* vol. 111, No. 5, pp. 406–416, 1999.

(Continued)

*Primary Examiner*—Bao-Thuy L. Nguyen
(74) *Attorney, Agent, or Firm*—Sughrue Mion, PLLC

(57) ABSTRACT

A diagnostic tool is disclosed for accurately and rapidly diagnosing the condition of an ailing organ. Although applicable to numerous organ and organ systems, this application particularly illustrates the concept of conjunctive marker utilization as it relates to diagnosing and distinguishing congestive heart failure. The invention particularly relates to the conjunctive utilization of cardiac Troponin I (cTn-I) and natriuretic peptide, e.g. ANP, pro-ANP, BNP, pro-BNP and CNP as a retrospective tool for diagnosing the underlying mechanism of heart failure and as a prospective analytical device for monitoring disease progression and efficacy of therapeutic agents.

17 Claims, No Drawings-

OTHER PUBLICATIONS

Moe et al., "Neurohormonal activation in severe heart failure: Relations to patient death and the effect of treatment with flosequinan," *Amer. Heart J.*, vol. 139, No. 4, pp. 588–595, 2000.

Maisel et al., "Utility of B–natriuretic peptide as a rapid, point–of–care test for screening patients undergoing echocardiography to determine left ventricular dysfunction," *Amer. Heart J.*, Mar. 2001, pp. 368–374.

Hammerer–Lercher et al., "Head–to head comparison of N–terminal pro–brain natriuretic peptide, brain natriuretic peptide and N–terminal pro–atrial natriuretic peptide in diagnosing left ventricular dysfunction," *Clinica Chmica Acta* 310, pp. 193–197, 2001.

ACC Clinical Data Standards—Am. College of Cardiology Key Data Elements and Definitions for Measuring the Clinical Management and Outcomes of Patients with Acute Coronary Syndromes, *J. Am. College of Cardiology*, vol. 38, No. 7, Dec. 2001, pp. 2114–2130.

Mair et al., "Natriuretic peptides in assessment of left–ventricular dysfunction," *Scan. J. Lab. Invest.* 1999;59 (Suppl 230), pp. 132–142.

Wu, "Analytical and clinical evaluation of new diagnostic tests for myocardial damage," *Clinica Chimica Acta* 272:11–21, 1998.

Prickett et al., "Identification of Amino–Terminal Pro–C–Type Natriuretic Peptide in Human Plasma," *Biochem. Biophys. Res. Commun.* 286:513–517. 2001.

Ricchiuti, et al., "Cardiac troponin T isoforms expressed in renal diseased skeletal muscle will not cause false–positive results by the second generation cardiac troponin T assay by Boehringer Mannheim,"*Clin. Chem.* 44:1919–1924, 1998.

Stein et al, "Natruiretic peptides: Physiology, therapeutic potential, and risk stratification in ischemic heart disease," *Amer. Heart J.* 135:914–923, 1998.

Ogawa et al., "Characterization of natriuretic peptide production by adult heart atria," *Am. J. Physiol.* 276:H1977–H1986, 1999.

Luchner et al., "Differential atrial and ventricular expression of myocardial BNP during evolution of heart failure," *Am. J. Physiol.*, 274:H1684–H1689, 1998.

Liew et al., "A catalogue of genes in the cardiovascular system as identified by expressed sequenced tags," *Proc. Natl. Acad. Sci. USA*, 91:10645–10649, 1994.

Yu et al., "Plasma brain natriuretic peptide—an independent predictor of cardiovascular mortality in acute heart failure," *Eur. J. Heart Fail.*, 1:59–65, 1999.

Sagnella et al., "Atrail natriuretic peptide in human plasma—comparison of radioreceptor versus radioimmunoassay," *Clinica Chimica Acta.* 166:37–44 1987.

Jancin, "Rapid test helps identify cause of dyspnea—point–of–care brain natriuretic peptide immunoassay," *Family Practice News,* May 1, 2000.

Apple et al., "Myocardial infarction redefined: Role of cardiac troponin testing," *Clin. Chem.* 47:377–379, 2001.

Ballerman, "A highly sensitive radioreceptor assay for atrial natriuretic peptide in rat plasma," *Amer. J. Physiol.* 254:F159–F163, 1988.

Bürgisser et al. "Human cardiac plasma concentrations of atrial natriuretic peptide quantified by radioreceptor assay;" 133:1201–1209, 1985.

Gutkowska et al., "Radioreceptor assay for atrial natriuretic factor," *Anal. Biochem.* 168:100–106, 1988.

Takemura et al., "Ventricular expression of atrial and brain natriuretic peptides in patients with nyocarditis," *Int. J. Cardiol.* 52:213–222, 1995.

Altemos et al., "Altered myocardial phenotype after mechanical support in human beings with advanced cardiomyopathy," *J. Heart Lung Transplant.*, 16:765–773, 1997.

Takemura et al., "Expression of atrial and brain natriuetic peptides and their genes in hearts of patients with cardiac amyloidosis," *JACC* 31:254–265, 1998.

Ziebig et al., Renal elimination of troponin T and Troponin I, *Clin. Chem.* 49:1191–1193, 2003.

Yasue, H., "Localization and Mechanism of Secretion of B–Type Natriuretic Peptide in Comparison with those of A–Type Natriuretic Peptide in Normal Subjects and Patients with Heart Failure," *Circulation*, vol. 90, No. 1, Jul. 1994, pp. 195–203.

Blomkalns, A. et al., "Markers and the Initial Triage and Treatment of Patients with Chest Pain," *Cardiovascular Toxicology*, vol. 1 No. 2 pp. 111–115, 2001.

Boomsma, F., "Plasma A– and B–type natriuretic peptides; Physiology, methodology and clinical use," *Cardiovascular Research*, 51 (2001) 442–449.

Donaldson, A., "Cardiac troponin levels in patients with impaired renal function," *Hospital Medicine*, Feb. 2001, vol. 62, No. 2, pp. 86–89.

McCullough, P., et al., "Risks Associated with Renal Dysfunction in Patients in the Coronary Care Unit," *J. Am. College of Cardiology*, vol. 36, No. 3, Sep. 2000, pp. 679–684.

Ni, Chen, "Cardiac Troponin 1: A Biomarker for Detection and Risk Stratification of Mino Myocardial Damage," *Clin. Lab*, vol. 47, 2001, pp. 483–492.

Villar–Palasi, et al., "Glycogen Metabolism and Glycolytic Enzymes," *Annual Review of Biochem.,* 1970, vol. 39, pp. 639–673.

Collision, P. et al., "Measurement of cardiac troponins," *Annals of Clinical Biochemistry*, 2001: 38 423–449.

Sundsfjord, J.A.:, et al., "Identification and Plasma Concentrations of the N–Terminal Fragment of Proatrial Natriuretic Factor in Man." *Clinical Endocrinology & Metabolism*, vol. 66, No. 3, Mar. 1988, pp. 605–610.

McCullough, P., et al, "Performance of Multiple Cardiac Biomarkers Measured in the Emergency Department in Patients with Chronic Kidney Disease and Chest Pain," *Acad Emerg Med*, vol. 9, No. 12, Dec. 2002, pp. 1389–1396.

Michener, M. t al., "Proteolytic Processing of Atriopeptin Prohormone," *Molecular Pharmacology*, vol. 30, No. 6 Dec. 1986 pp. 552–557.

Needleman, P., et al "Atriopeptins as Cardiac Hormones," *Hypertension*, vol. 7, No. 4, Jul.–Aug. 1985 pp. 469–482.

Mantymaa, P., "Atrial Stretch Induces Rapid Increase in Brain Natriuretic Peptide but not in Atrial Natriuretic Peptide Gene Expression in Vitro," *Endocrinology*, vol. 133, No. 3, pp. 1470–1473.

Ikram et al., "An ovine model of acute myocardial infarction and chronic left ventricular dysfunction," *Angiology*, vol. 48(8) Aug. 1997 pp. 679–688.

Ogawa, Y et al., "Molecular Biology and Biochemistry of Natriuretic Peptide Family," *Clin. And Experi. Pharm. And Phy.*, vol. 22, 1995 pp. 49–53.

Kelly, R. et al, "Are natriuretic peptides clinically useful as markers of heart failure," *Ann Clin Biochem*, 2001: 38: 94–102.

Zoccali, C. et al, "Cardiac Natriuretic Peptides Are Related to Left Ventricular Mass and Function and Predict Mortality in Dialysis Patients," *J. Am Soc Nephrol*, 12: 2001 1508–1515.
Yoshimura, M. et al., "Interaction on Metabolic Clearance Between A–Type and B–Type Natriuretic Peptides in Patients with Heart Failure," *Metabolism*, vol. 49, No. 9 Sep. 2000, pp. 1228–1233.
Selvais, P.L.., et al "Cardiac natriuretic peptides for diagnosis and risk stratification in heart failure: influences of left ventricular dysfunction and coronary artery disease on cardiac hormonal activiation," *European J. of Clinical Investigation*, (1998) 28, 636–642.
Selvais, P.L., et al., "Direct Comparison Between Endothelin–1, N–Terminal Proatrial Natriuretic Factor, and Brain Natriuretic Peptide as Prognostic Markers of Survival in Congestive Heart Failure," *J of Cardiac Failure* vol. 6, No. 3 2000 pp. 201–206.
Richards, A.M., "Neuroendocrine prediction of left ventricular function and heart failure after acute myocardial infarction," *Heart*, vol. 81, 1999, pp. 114–120.
Omland, T., et. Al., "Plasma Brain Natriuretic Peptide as an Indicator of Left Ventricular Systolic Function and Long–term Survival after Acute Myocardial Infarction," *Circulation*, vol. 93, No. 11, Jun. 1996 pp. 1963–1969.
Arakawa, N., et al., "Plasma Brain Natriuretic Peptide Concentration Predict Survival After Acute Myocardial Infarction," *JACC*, vol. 27, No. 7, Jun. 1996 pp. 1656–1661.
Darbar, D., et al., "Diagnostic Value of B–Type Natriuretic Peptide Concentrations in Patients with Acute Myocardial Infarction," *Am J of Cardiology*, vol. 78 Aug. 1996 pp. 284–287.
Horio, T., et al., "Serial changes in atrial and brain natriuretic peptides in patients with acute myocardial infarction treated with early coronary angioplasty," *Am Heart Journal*, vol. 126, No. 2 Aug. 1993 pp. 293–299.
Maeda, K., et al., "High levels of Plasma Brain Natriuretic Peptide and Interleukin–6 After Optimized Treatment for Heart Failure are Independent Risk Factos for Morbidity and Mortality in Patients with Congestive Heart Failure," *J of Am College of Cardiology*, vol. 36, No. 5 2000 pp. 1587–1593.
Nagaya, et al., "Plasma Brain Natriuretic Peptide as a Prognostic Indictor in Patients with Primary Pulmonary Hypertension," *Circulation*, Aug. 22, 2000 pp. 865–870.
Stanton et al., "Cardiac troponin I, a possible predictor of survival in patients with stable congestive heart failure," *Can. J. Cardiol.*, 21:39–43, 2005.
Wright et al., "Amino–Terminal Pro–C–Type Natriuretic Peptide in Heart Failure," *Hypertension*, 43:94–100, 2004.

CONJUNCTIVE ANALYSIS OF BIOLOGICAL MARKER EXPRESSION FOR PREDICTING CARDIAC MORTALITY

Matter enclosed in heavy brackets [ ] appears in the original patent but forms no part of this reissue specification; matter printed in italics indicates the additions made by reissue.

*This is a reissue of U.S. Pat. No. 6,461,828, which issued from application Ser. No. 09/946,171, filed Sep. 4, 2001.*

FIELD OF THE INVENTION

This invention relates to the concept of conjunctive utilization of biological markers expressed in response to abnormal pressure, volume change and stress to a particular organ (e.g. N-terminal ANP (pro-ANP) in heart tissue) along with the expression of biological markers that are indicative of tissue damage (e.g. cardiac Troponin I (cTnI), or fibrosis markers for heart tissue) as a diagnostic tool to accurately and rapidly diagnose the condition of the ailing organ. Although this concept is applicable to numerous organ and organ systems, this application will particularly illustrate the concept of conjunctive marker utilization with respect to the heart, specifically with respect to congestive heart failure. The invention particularly relates to the conjunctive utilization of cardiac Troponin I (cTnI) and natriuretic peptides, e.g. brain natriuretic peptide (BNP), N-terminai BNP (pro-BNP)), c-type natriuretic peptide (CNP), atrial natriuretic peptide (ANP), and N-terminal ANP (pro-ANP) as a retrospective tool for diagnosing the underlying mechanism of heart failure and as a prospective analytical device for monitoring disease progression and efficacy of therapeutic agents.

BACKGROUND OF THE INVENTION

Congestive heart failure (CHF) effects approximately 4.8 million Americans. About 400,000 new cases are diagnosed annually and the condition is responsible for approximately 200,000 deaths per year. These statistics, in conjunction with the approximately;1 million hospitalizations annually attributable to CHF, result in an annual expenditure on the order of $10 billion.

CHF represents a condition which occurs when heart function becomes insufficient to meet the needs of the vital systems and tissues of the body. The inability of the heart to pump sufficiently is correlated to the measured ejection fraction, which is the percent of the blood pumped out during each heartbeat. An ejection fraction of between 50% and 75% is considered normal. This inability can be caused by failure of one or more sides of the heart, typically the left but also the right side; such failure can result from systolic or diastolic dysfunction, and may be represented by an ejection fraction of less than 50% and a resultant backup of fluid and accumulation of fluid in the lungs. Although less common, right-sided heart failure will result in fluid backup that manifests in a swelling of the veins and surrounding body tissues, inadequate tissue perfusion, fatigue and poor exercise tolerance. In addition, heart failure can result from diastolic dysfunction. This can result from disorders such as hypertension, valvular disease, transient ischemia, infiltrative disorders or congenital conditions such as hypertrophic cardiomyopathy. Although there are cases of pure diastolic dysfunction from infiltrative disorders such as amyloidosis or fibrosis, heart failure patients often have a combination of both systolic and diastolic dysfunction contributing to CHF.

The underlying reasons for this failure in heart functionality are varied. Thinning and weakening of the ventricle walls leads to dilation and a loss of pumping ability (systolic dysfunction). Alternatively, loss of elasticity results in a stiffening, which may result in a diminished volume of the heart's chambers and loss of pumping capacity (diastolic dysfunction) and cardiac output. Additionally, abnormalities in the functioning of the heart's valves can lead to insufficient cardiac output, for which the body attempts to compensate by causing the heart to increase its heart rate, hypertrophy and/or dilate. The compensation mechanisms utilized by the body may lead to architectural changes in the form of remodeling (especially after MI) or adaptation of the heart muscle, ultimately leading to irrevocable loss of function. Related causes of cardiac failure may be one or more conditions such as coronary artery disease, ischemic heart damage, e.g. damage resulting from a heart attack, uncontrolled hypertension, the direct and/or indirect effects of diabetes on the heart, valvular heart disease, cardiomyopathy, autoimmune response, disease and abuse by external agents such as alcohol, tobacco, anabolic steroids, and the like.

Historically, the preliminary diagnosis of CHF requires a history and a physical examination during which the condition is often characterized by various signs and symptoms of intra-vascular and interstitial volume overload, including shortness of breath, irregular heart rate, abnormal heart rate and signs of edema. To determine the severity and prognosis of CHF and to more clearly characterize a particular patient's condition, further diagnostic tests are usually needed.

Tests which further illustrate the mechanical condition of the heart are often useful, such tests include, but are not limited to, exercise stress testing, electrocardiogram, radionucleidangiography, echocardiography, chest X-ray and angiography. Echocardiography is presently considered an important diagnostic test for CHF. By using ultrasound to provide real time imagery of the beating heart, valve function and blood flow through the heart can be readily ascertained. Systolic function and diastolic function or some combination thereof is determinable through echocardiography.

Laboratory tests including but not limited to blood and urine testing are often helpful. These may indicate abnormalities in liver function, kidney function, cholesterol levels; blood sugar levels, hemoglobin levels, thyroid hormone levels and ANP, BNP, pro ANP, pro-BNP.

The diagnostic methods for diagnosing and distinguishing CHF, as outlined above, require numerous steps, expensive technology, and trained personnel for their performance and subsequent analysis. Patients may also be exposed to risk of radiation from nuclear studies or invasive procedures, i.e. heart catheterization. If a method and device could be provided for distinguishing and diagnosing CHF via a simplified body fluid test, the results of which could be interpreted by a lay person, a long felt need would be satisfied.

DESCRIPTION OF THE PRIOR ART

It is well documented in the literature that several peptides exist in the atrium of the human heart which possess the ability to regulate normal extra-cellular fluid parameters including volume and pressure of liquid in blood vessels. These peptides are referred to as Atrial Natriuretic Peptides (ANP). Brain natriuretic peptide or BNP is a peptide isolated initially from pig brain and hence the name BNP (Sudoh et al., Nature, 332:78–81, 1988). In humans, this peptide is synthesized by the brain and myocardial cells and circulates in the bloodstream exerting profound influences on the heart and kidneys. BNP is structurally related to the ANP family of peptides and is present in significantly lower quantities in circulation. The appearance of pro-BNP has been correlated with the progression of heart failure. However, the active molecule is BNP which has been found to be beneficial to the failing heart. It is conceivable that the damage to heart muscle may result in an inefficient processing of the inactive pro-BNP to active BNP (which accounts for the observed increase in pro-BNP). However, due to the inability of the cardiac tissues to process the pro-BNP to BNP, there is no beneficial effect unless the active molecule (BNP) is administered externally.

In addition to changes in pro-BNP/BNP during heart failure, an increase in cardiac Troponin I correlates well with cardiac tissue damage and appears to be a good predictor of death due to cardiac failure. During cardiac cell damage and death, cellular contents are released into the blood stream. Cardiac Troponin I has been shown to be a specific diagnostic marker of cardiac cell damage (Circulation 83, 902–912(1991); Clin. Chem. 40, 1291–1295(1994); Clin. Chem. 41, 312–317 (1995)).

U.S. Pat. No. 6,162,902 entitled "Human BNP-Specific Antibodies" provides reagents and assays for the quantification of hBNP in biological fluid samples such as plasma or serum.

U.S. Pat. No. 5,795,725 entitled "Methods for the Assay of Troponin I and T and Selection of Autoantibodies for use in Immunoassays" discloses assays and antibodies for detection and quantitation of cardiac specific Troponin I and Troponin T in body fluids as an indicator of myocardial infarction.

The present inventor has previously obtained U.S. Pat. Nos. 5,747,274 and 5,604,105, entitled "Method and Device for Diagnosing and Distinguishing Chest Pain in Early Onset Thereof", the contents of which is hereby incorporated by reference. The '274 patent teaches a diagnostic test, and a device for conducting the test, for assessing whether patient chest pain is cardiac in origin and for differentiating between unstable angina and myocardial infarction as a cause of patient chest pain. The diagnostic test comprises simultaneously detecting at least three selected cardiac markers with the use of at least three different monoclonal or polycional antibody pairs, each member of which is complementary to a different marker, which is released by heart muscle at varying stages after the onset of chest pain and is indicative of the cause of the chest pain. Troponin-I is disclosed as a cardiac specific ischemic marker.

Additionally, U.S. Pat. No. 5,290,678 to Jackowski entitled "Diagnostic Kit for Diagnosing and Distinguishing Chest Pain in Early Onset Thereof", the contents of which is further incorporated by reference herein, discloses a diagnostic test kit for assessing whether patient chest pain is cardiac in origin and for differentiating between unstable angina and myocardial infarction at early onset of patient chest pain. The test kit comprises a receptacle for receiving and retaining a sample of blood or serum of the patient and at least three monoclonal or polyclonal antibodies suspended on a carrier. Each antibody is complementary to a different protein released by the heart muscle during early stages of a myocardial infarction and has corresponding reagents which are independently responsive to each antibody reacting the complementary protein. The combined response of reagents indicates the diagnostic condition of the patient.

The prior art fails to teach or suggest the combined use of a cell injury marker, e.g. cardiac Troponin-I and a marker related to volume or pressure overload, e.g. an adaptation marker such as a natriuretic peptide, e.g. pro-ANP, to provide a testing device for predicting and/or distinguishing congestive heart failure, nor does it suggest that the combination of these biological markers could provide both a retrospective tool for diagnosing the underlying mechanism of heart failure and a prospective analytical device for monitoring disease progression and efficacy of therapeutic agents.

SUMMARY OF THE INVENTION

The present invention reduces to practice the concept of conjunctive utilization of markers that indicate pressure, volume change and stress to a particular organ (e.g. pro-ANP in heart tissue) along with markers that are indicative of tissue damage (e.g. cardiac Troponin I for heart tissue) as well as markers of fibrosis, as a diagnostic tool to accurately and rapidly diagnose the condition of the ailing organ. Although this concept is applicable to numerous organ and organ systems, this application will illustrate the concept of conjunctive marker utilization with respect to the heart.

Cardiac Troponin I and BNP (pro-BNP) have previously been utilized as markers indicative of cardiac tissue damage and pressure, volume overload and stress to the heart, respectively. However, neither these molecules nor any other natriuretic peptide, e.g. pro-ANP, have been used in conjunction as a diagnostic tool to accurately and rapidly diagnose the condition of the ailing heart.

The instant invention provides the scientific basis for the development of an immunological test that has the potential to 1) replace expensive and time-consuming imaging techniques so that the appropriate therapeutic intervention may be afforded to the patient soon after arrival into the emergency room, and 2) provide a simplified means for diagnosing, distinguishing and quantifying chronic heart failure and the treatment thereof.

While the examples presented herein are for the heart, the innovative concept of utilizing biochemical markers to distinguish tissue damage from adaptive mechanisms is applicable to almost any organ including, but not limited to, the brain, kidneys, the adrenal glands, pancreas, lungs, eyes and the liver.

In accordance with this invention the term "cell injury" is defined as including any transient impairment of cell function, and/or cell death or necrosis as a result of insult or apoptosis.

In accordance with this invention, the term "organ adaptation" refers to changes in the organ as a result of or in response to pressure or volume overload stretch, hypertrophy, wall stress, and the like physiological factors which stress the organ.

A remodeling including myocardial fibrosis (increased cTnI) or adaptation (increased natriuretic peptide) of the heart muscle may accompany progression in CHF. Currently, all these changes to the heart are evident only with the use of expensive heart imaging techniques.

Accordingly, it is an objective of the instant invention to provide an analytical test, either via a central laboratory, or point-of-care test, e.g. a rapid format test, performed on a biological fluid for diagnosing congestive heart failure, the result of said test being readily ascertainable without special training.

It is a further objective of the instant invention to provide a test capable of ruling out high risk patients with congestive heart failure, and thereby permitting the most efficient use of medical resources.

It is yet another objective of the instant invention to describe a test which exhibits improved diagnostic accuracy over clinical evaluation.

It is a still further objective of the invention to provide a test for detecting pre-clinical disease.

It is yet an additional objective of the instant invention to provide a test which confirms cardiac etiology of symptoms, reduces the need for cardiac imaging, yields data for determining long term management and monitoring, and serves as a predictor of mortality.

It is yet a further objective of the instant invention to provide a testing device useful in targeting titration of therapies, e.g. utilization of ACE inhibitors vasodilators, diuretics and the like; said test being indicative of the prognostic efficacy of said therapies.

Other objects and advantages of this invention will become apparent from the following description taken in conjunction with the accompanying drawings wherein are set forth, by way of illustration and example, certain embodiments of this invention.

DETAILED DESCRIPTION OF THE INVENTION

It has been known for many years that during a cardiac event, heart tissue releases certain molecules, typically protein molecules which are characteristic of the event. Certain of them are released as a result of both UA and MI, others are released as a result of MI. It has been suggested that these markers, often called analytes, be employed in antigen/antibody reactions to recognize the cause of a cardiac event.

Sensitivity and Specificity

"Sensitivity" as used herein refers to the ability of an antibody to recognize and react with its analyte antigen when the analyte is present at very low concentration in a mixture, i.e., blood, serum, plasma or other blood preparation when that mixture contains relatively large numbers of other components. Sensitivity in antigen/antibody reactions is achieved principally by using antibodies with high affinity for their antigens.

"Specificity" as used herein refers (a) to the specificity of an antibody for an analyte, i.e., there is no, or minimal, cross reaction of the antibody with other materials in the sample under test; and (b) to the specificity of the source of the antibody, i.e., did it originate in heart tissue or some other tissue and therefore facilitate diagnosis.

These different types of sensitivity will be referred to herein as "cell injury sensitivity," i.e., the antibodies recognize cell injury markers and "organ adaptation sensitivity," i.e., the antibodies originate from a specific tissue and therefore permit a correct and prompt diagnosis. In other words, they are tissue specific. If they originate only from heart tissue, they are cardiac specific.

Many markers are known to which antibodies, either monoclonal or polyclonal, have been produced or can be produced by procedures well known to the skilled artisan. Many of them are not tissue specific. They originate not only in heart tissue but also in muscle or other body tissue. Their tissue sensitivity is not cardiac sensitivity.

The tests according to the invention can be performed at the point of care by medically trained personnel. For example, emergency medical service workers can perform a test of the invention at the site of a medical emergency or in the ambulance on the way to the hospital. Similarly, medical personal in the emergency room, cardiac care facility or other point of care location at a hospital can perform a test of the invention themselves. Naturally and where clinically appropriate, the patient sample such as blood or any blood product, plasma, or serum, or urine may be provided to a hospital laboratory to perform the test.

The invention extends to test materials including reagents in a kit form for the practice of the inventive method. The materials comprise the binding partners that are specific to the markers under detection, and in one embodiment, comprise the antibody or antibodies, each of which is specific for one of each of the markers, the presence of which is to be determined.

In an illustrative embodiment, one antibody of each pair specific for a particular marker is irreversibly immobilized onto a solid support; this antibody is alternately referred to hereinafter as a capture antibody. The other antibody specific for the same marker is labeled, and is capable of moving with a sample to the location on the solid support of the capture antibody. This antibody is sometimes referred to herein as the detection antibody.

The present invention correspondingly extends to devices for conducting the assays, i.e., a device for early determination of the presence of congestive heart failure. According to one aspect of this embodiment of the invention there is provided a device comprising a housing means containing a membrane unit or section, with a detector section and a capture section, preferably with a filter section. The detector section contains at least one detector antibodies specific to an epitope on each of the markers to be tested for in a patient's sample of blood, serum or plasma. The capture section contains at least one capture antibodies specific to another epitope of each of the markers to be detected. The capture section is positioned distal to the position of the detector section, wherein the capture antibodies are irreversibly immobilized in the capture section, the detector antibodies are reversibly immobilized in the detector section and migrate with the sample into the capture section, when the device is in use. The detector antibodies may be suitably labeled to give a measurable reaction when the marker is present and is bound in accordance with the process of this invention.

Binding of the binding partner or antibody to its cognate antigen, the marker, in a sample can be detected by other detection means, such as optical detection, biosensors, homogenous immunoassay formats, and the like. Particular optical sensing systems and corresponding devices are contemplated and are discussed in U.S. Pat. 5,290,678.

As used herein, the term "marker" refers to a protein or other molecule that is released from an organ during a cell injury event or an organ adaptation event. Such markers include, but are not limited to, proteins or isoforms of proteins that are either unique to the heart muscle, and/or proteins or isoforms thereof that are found in tissues other than heart muscle.

The markers of the present invention are released into the blood. Thus, the invention contemplates assessing the level of the markers in blood, or any blood product that contains them such as, but not limited to, plasma, serum, cytolyzed blood (e.g., by treatment with hypotonic buffer or detergents; see, e.g., International Patent Publication No. WO 92/08981, published May 29, 1992), and dilutions and preparations thereof.

The term "above normal" or "above threshold" are used herein to refer to a level of a marker that is greater than the level of the marker observed in normal individuals. For some markers, no or infinitesimally low levels of the markers may be present. For other markers, detectable levels may be present normally in blood. Thus, the terms further contemplate a level that is significantly above the level found in patients. The term "significantly" refers to statistical significance, and generally means at least a two-fold greater level of the marker is present. However, a significant difference between levels of markers depends on the sensitivity of the assay employed, and must be taken into account for each marker assay.

The markers which can be used according to the present invention are any molecules, typically proteins that pass out from the organ's cells as the cells become damaged or as adaptation occurs. These proteins can be either in the native form or can be immunologically detectable fragments of the protein, resulting, for example, from photolytic digestion of the protein. When the terms "marker" or "analyte" are used, they are intended to include fragments thereof that can be immunologically detected. By "immunologically detectable" is meant that the protein fragments contain an epitope that is specifically recognized by a cognate antibody. Examples of cell injury/necrosis markers are listed below in Table 1.

TABLE 1

| |
|---|
| Troponin-T |
| Troponin-I |
| MLC-1 |
| MLC-2 |
| Glycogen Phosphorylase BB |
| Ca ATPase |
| Phospholamben |
| Myosin Heavy Chain |
| Actin |
| Tropomyosin |
| Calmodulin |
| Caldermon |
| Phospholamben phosphate |
| Calsequestrin |
| $Ca^{++}$ pumping adenosine triphosphatase |
| $Ca^{++}$ transport ATPase |
| Adenylate cyclase |
| Protein kinase |
| Histidine rich calcium binding protein |
| Protein phosphatase |
| Protein phosphatase 2C |
| High affinity calcium binding protein |
| Low density lipoprotein-binding sarcoplasmic reticulum protein |
| $Ca^{++}$-requiring protease (m-calpsin) |
| Pyruvate dehydrogenease |

EXAMPLE

Cardiac troponin I (cTnI) has been validated as a sensitive and specific marker of myocyte damage and as a predictor of adverse events in acute coronary syndromes cTnI has been also reported to be elevated in patients with congestive heart failure. Similarly, pro-ANP has been reported to be elevated in patients with CHF. Congestive heart failure is characterized by hemodynamic and neurohumoral responses to injury that result in progressive cardiac remodeling, fibrosis and apoptosis. However in patients with chronic heart failure, it is unclear whether there is a relationship between either elevated levels of cTnI alone, or in conjunction with elevated levels of pro-ANP, and survival. We thus assessed whether detectable levels of cTnI was associated with survival in 221 chronic heart failure patients. In addition, we assessed whether cTnI levels in conjunction with pro-ANP levels was more predictive of survival than each marker individually. These patients were categorized as Class III or Class IV by NYHA standards. Criteria for inclusion in the study were: symptomatic heart failure of New York Heart Association (NYHA) class III and IV; left ventricular ejection fraction ≦35% by radionuclide ventriculography or echocardiography; treatment with digitalis, diuretics, and angiotensin-converting enzyme inhibitors ≧60 days; and informed consent. Criteria for exclusion were restrictive cardiomyopathy, primary valvular heart disease, consideration for heart transplantation, history of acute myocardial infarction, coronary artery bypass graft surgery or other cardiac surgery ≦60 days, symptom-limiting unstable angina or angina attacks ≧3 per week, and history of symptomatic ventricular arrhythmias. Additional exclusion criteria were ongoing type I anti-arrhythmic therapy, concomitant use of calcium-channel blockers or Hydralazine, use of inhaled β-agonists ≧once per week, use of oral or intravenous non-digitalis inotropes more than one week before the baseline assessment, severe pulmonary or other systemic diseases, hepatic enzymes more than 2 times the upper limit of normal, and a serum creatinine ≧270μmol/L. Conjunctive analysis of cTnI and pro-ANP yielded the following results.

Congestive Heart Failure[1]: Cardiac Mortality Rates Based Upon ANP[2] and cTnI[3] Levels

| | *ANP +ve | cTnI +ve | **ANP −ve/cTnI −ve |
|---|---|---|---|
| Deceased | 18 (29%) | 10 (38%) | 18 (13%) |
| Alive | 44 (71%) | 16 (62%) | 124 (87%) |

Statistics
1. ANP +ve vs. ANP −ve/cTnI −ve Pearson chi-square = 7.944 p = 0.0048 RR = 1.91 (CI 1.262-2.887)
2. cTnI +ve vs. ANP −ve/cTnI −ve Pearson chi-square = 10.52 p = 0.0011 RR = 3.13 (CI 1.586-6.1558)
3. cTnI +ve vs. ANP +ve Pearson chi-square = 1.818 p = 0.1775

| | *ANP +ve/ cTnI +ve | **ANP −ve/ cTnI −ve | ANP +ve/ cTnI −ve | ANP −ve/ cTnI +ve |
|---|---|---|---|---|
| Deceased | 5 (55%) | 18 (13%) | 13 (24%) | 5 (29%) |
| Alive | 4 (45%) | 124 (87%) | 40 (76%) | 12 (71%) |

Statistics
1. ANP +ve/cTnI +ve vs. ANP −ve/cTnI −ve Pearson chi-square = 12.052 p = 0.0005 RR = 6.96 (CI 2.018-23.983)
2. ANP +ve/cTnI +ve vs. ANP +ve/cTnI −ve Pearson chi-square = 3.59 p = 0.0579 RR = 3.06 (CI 0.925-10.094)
3. ANP +ve/cTnI +ve vs. ANP −ve/cTnI +ve Pearson chi-square = 1.699 p = 0.1923
4. ANP +ve/cTnI −ve vs. ANP −ve/cTnI −ve Pearson chi-square = 4.055 p = 0.0440 RR = 1.72 (CI 1.0489-2.818)
5. ANP −ve/cTnI +ve vs. ANP −ve/cTnI −Pearson chi-square = 3.437 p = 0.0637 RR = 2.46 (CI 0.9881-6.3393)

*ANP ≧ 3000 pmol/L cTnI +ve - ≧0.1 ug/L
**ANP < 3000 pmol/L cTnI +ve - <0.1 ug/L
[1]Class III and IV Heart Failure
[2]N-terminal Atrial Natriuretic Peptide
[3]Cardiac Troponin I We have performed a simple linear regression analysis of cTnI levels on pro-ANP levels. We found that the R2 value for two separate experiments and their combination was 0.0002. F ration for the model was 0.06. The probability associated with the model was 0.80. Thus we found no evidence that cTnI levels were significantly dependent on pro-ANP levels.

cTnI and pro-ANP levels are therefore deemed to be independent of each other in predicting mortality rates as per the linear regression analysis, and it is concluded that more prognostic information related to CHF can be garnered by looking at the markers conjunctively as opposed to individually.

As used herein, the term antibody includes polyclonal and monoclonal antibodies of any isotype (IgA, IgG, IgE, IgD, IgM), or an antigen-binding portion thereof, including but not limited to F(ab) and Fv fragments, single chain antibodies, chimeric antibodies, humanized antibodies, and a Fab expression library.

Antibodies useful as detector and capture antibodies in the present invention, may be prepared by standard techniques well known in the art. The antibodies can be used in any type of immunoassay. This includes both the two-site sandwich assay and the single site immunoassay of the non-competitive type, as well as in traditional competitive binding assays.

Particularly preferred, for ease and simplicity of detection, and its quantitative nature, is the sandwich or double antibody assay of which a number of variations exist, all of which are contemplated by the present invention. For example, in a typical sandwich assay, unlabeled antibody is immobilized on a solid phase, e.g. microtiter plate, and the sample to be tested is added. After a certain period of incubation to allow formation of an antibody-antigen complex, a second antibody, labeled with a reporter molecule capable of inducing a detectable signal, is added and incubation is continued to allow sufficient time for binding with the antigen at a different site, resulting with a formation of a complex of antibody-antigen-labeled antibody. The presence of the antigen is determined by observation of a signal which may be quantitated by comparison with control samples containing known amounts of antigen.

The assays may be competitive assays, sandwich assays, and the label may be selected from the group of well-known labels such as radioimmunoassay, fluorescent or chemiluminescence immunoassay, or immunoPCR technology. Extensive discussion of the known immunoassay techniques is not required here since these are known to those of skilled in the art. See Takahashi et al. (Clin Chem 1999;45(8):1307) for S100B assay.

Although not wishing to be limited to any particular embodiment, the panel format exemplified herein is known and is commercially available. The panel format is similar to a format currently being used in association with pregnancy testing and is commercially available under the trade-mark BIOSIGN.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification.

One skilled in the art will readily appreciate that the present invention is well adapted to carry out the objectives and obtain the ends and advantages mentioned, as well as those inherent therein. The various biomolecules, e.g. antibodies, markers, oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

[1. A method for predicting cardiac mortality rate in a patient, said method comprising the steps of:

drawing a sample of serum or plasma from a patient, depositing the sample in a sample window of a diagnostic test kit, said test kit comprising a front panel comprising a sample window and a display window;

a back panel; and a dry chemistry membrane affixed between the front and back panels positioned for display in at least the display window, wherein said membrane comprises:

a sample region, and a control region, said sample region positioned to receive the sample from the sample window; and at least two antibody pairs located at discrete locations along said membrane between the sample region and the control region, each of said antibody pairs comprising an antibody reagent member and an immobilized capture antibody member, each capture antibody member being located on said membrane closer to the control region than the corresponding antibody reagent member, each antibody pair having a measurable or observable moiety labeled or chemically bonded to the antibody reagent member of each said antibody pairs, the antibody pairs being monoclonal or polyclonal and comprising:

a first antibody pair that specifically binds to a marker of cell injury selected from the group consisting of Troponin-T, cardiac Troponin-I, MLC-1, MLC-2, Glycogen Phosphorylase BB, Ca ATPase, Phospholamban, Myosin Heavy Chain, Actin, Tropomyosin, Calmodulin, Caldosmon Phospholamban phosphatase Calsequestrin, $Ca^{++}$ pumping adenosine triphosphatase, $Ca^{++}$ transport ATPase, Adenylate cyclase, Protein kinase, Histidine rich calcium binding protein, Protein phosphatase, Protein phosphatase 2C, High affinity calcium binding protein, Low density lipoprotein-binding sarcoplasmic reticulum protein, $Ca^{++}$-requiring protease (m-calpain), and Pyruvate dehydrogenase, and a second antibody pair that specifically bind to a marker of organ adaptation selected from the group consisting of ANP, pro-ANP, BNP, pro-BNP and CNP, such that upon adding sample to the sample window, analytes present in the sample and complementary to the antibody pairs will migrate toward the control region, binding to the antibody pair each of said analytes, producing a color change proportional to each concentration of analyte present, and visualizing or measuring the moiety and determining cardiac mortality rate.]

[2. The method in accordance with claim 1 wherein:

the marker of cell injury is cardiac Troponin-I; and the marker of organ adaptation is atrial natriuretic peptide or pro-atrial natriuretic peptide.]

[3. The method of claim 1 wherein:

said body fluid is selected from the group consisting of blood, a blood product, plasma, serum, or urine.]

[4. A method for predicting cardiac mortality rate in a patient, said method comprising the steps of:

drawing a sample of a body fluid from a patient, contacting said sample with a first antibody that specifically binds to a marker of cell injury selected from the group consisting of Troponin-T, cardiac Troponin-I, MLC-1, MLC-2, Glycogen Phosphorylase BB, Ca ATPase, Phospholamban, Myosin Heavy Chain, Actin, Tropomyosin, Calmodulin, Caldesmon Phospholaiban phosphatase Calsequestrin, $Ca^{++}$ pumping adenosine triphosphatase, $Ca^{++}$ transport ATPase, Adenylate cyclase, Protein kinase, Histidine rich calcium binding protein, Protein phosphatase, Protein phosphatase 2C, High affinity calcium binding protein, Low density lipoprotein-binding sarcoplasmic reticulum protein, $Ca^{++}$-requiring protease (m-calpain), and Pyruvate dehydrogenase, contacting said sample with a second antibody that specifically binds to a marker of organ adaptation selected from the group consisting of ANP, pro-ANP, BNP, pro-BNP and CNP, and providing means for determining binding between each of said respective markers and each of said respective antibodies, whereby said binding provides a means for determining cardiac mortality rate.]

[5. The method of claim 4 wherein:

said body fluid is selected from the group consisting of blood, a blood product, plasma, serum, or urine.]

*6. A method for determining a relative risk of cardiac mortality in a chronic congestive heart failure patient, said method comprising the steps of:*

*(A) drawing a sample of a body fluid from said patient,*

*(B) assaying for the presence of a cardiac marker of cell injury in said sample using:*

*a first antibody that specifically binds to a cardiac marker of cell injury, wherein said cardiac marker of cell injury is selected from the group consisting of cardiac Troponin-T, cardiac Troponin-I, MLC-1, and MLC-2; and*

*(C) assaying for the presence of a marker of organ adaptation in a body fluid sample drawn from said patient using:*

*a second antibody that specifically binds to said marker of organ adaptation, wherein said marker of organ adaptation is selected from the group consisting of ANP, N-terminal ANP, BNP, N-terminal BNP and CNP,*

*wherein when both said marker of cell injury and said marker of organ adaptation are present in said sample at increased levels as compared to control samples, said patient has a greater risk of cardiac mortality.*

*7. The method of claim 6, wherein said body fluid is selected from the group consisting of blood, a blood product, plasma, serum, or urine.*

*8. The method of claim 7, wherein said body fluid is serum or plasma.*

*9. The method of claim 7 or 8, wherein:*

*said first antibody specifically binds to a cardiac marker of cell injury selected from the group consisting of cardiac Troponin-T and cardiac Troponin-I; and*

*said second antibody specifically binds to a marker of organ adaptation selected from the group consisting of BNP and N-terminal BNP.*

*10. The method of claim 9, wherein:*

*said first antibody specifically binds to cardiac Troponin-I and said second antibody specifically binds to N-terminal BNP.*

*11. The method of claim 6, 7 or 8, wherein both said assaying for the presence of a cardiac marker and said assaying for the presence of a marker of organ adaptation, comprise the steps of:*

*(a) depositing said sample in a sample window of a diagnostic test kit,*

*wherein said test kit comprises a front panel comprising the sample window and a display window; a back panel; and a dry chemistry membrane affixed between the front and back panels positioned for display in at least the display window,*

*wherein said membrane comprises:*

*a sample region positioned to receive the sample from the sample window,*

*a control region, and*

*at least a first antibody pair and a second antibody pair located at discrete locations along said membrane between the sample region and the control region,*

*each of said antibody pairs comprising an antibody reagent member and an immobilized capture antibody member, each capture antibody member being located on said membrane closer to the control region than the corresponding antibody reagent member, each antibody reagent member having a measurable or observable moiety labeled or chemically bonded thereto, wherein the antibody reagent member of said first antibody pair is said first antibody that specifically binds a cardiac marker of cell injury, and the antibody reagent member of said second antibody pair is said second antibody that specifically binds a marker of organ adaptation,*

*such that the cardiac marker of cell injury and the marker of organ adaptation present in the sample will migrate toward the control region, bind to a cognate antibody pair to form an immobilized immunocomplex, and produce a color change proportional to the concentration of each marker in the sample, and*

*(b) visualizing or measuring the moiety labeled or chemically bonded to said first antibody and said second antibody so as to detect the presence of each marker in said sample.*

*12. The method of claim 9, wherein both said assaying for the presence of a cardiac marker and said assaying for the presence of a marker of organ adaptation, comprise the steps of:*

*(a) depositing said sample in a sample window of a diagnostic test kit,*

*wherein said test kit comprises a front panel comprising the sample window and a display window; a back panel; and a dry chemistry membrane affixed between the front and back panels positioned for display in at least the display window,*

*wherein said membrane comprises:*

*a sample region positioned to receive the sample from the sample window,*

*a control region, and*

*at least a first antibody pair and a second antibody pair located at discrete locations along said membrane between the sample region and the control region,*

*each of said antibody pairs comprising an antibody reagent member and an immobilized capture antibody member, each capture antibody member being located on said membrane closer to the control region than the corresponding antibody reagent member, each antibody reagent member having a measurable or observable moiety labeled or chemically bonded thereto, wherein the antibody reagent member of said first antibody pair is said first antibody that specifically binds cardiac Troponin-T or cardiac Troponin-I and the antibody reagent member of said second antibody pair is said second antibody that specifically binds BNP or N-terminal BNP,*

*such that the cardiac marker of cell injury and the marker of organ adaptation present in the sample will migrate toward the control region, bind to a cognate antibody pair to form an immobilized immunocomplex, and produce a color change proportional to the concentration of each marker in the sample, and*

*(b) visualizing or measuring the moiety labeled or chemically bonded to said first antibody and said second antibody so as to detect the presence of each marker in said sample.*

*13. The method of claim 10, wherein both said assaying for the presence of a cardiac marker and said assaying for the presence of a marker of organ adaptation, comprise the steps of:*

*(a) depositing said sample in a sample window of a diagnostic test kit,*

*wherein said test kit comprises a front panel comprising the sample window and a display window; a back panel; and a dry chemistry membrane affixed between the front and back panels positioned for display in at least the display window,*

*wherein said membrane comprises:*

*a sample region positioned to receive the sample from the sample window,*

*a control region, and*

*at least a first antibody pair and a second antibody pair located at discrete locations along said membrane between the sample region and the control region,*

*each of said antibody pairs comprising an antibody reagent member and an immobilized capture antibody member, each capture antibody member being located on said membrane closer to the control region than the corresponding antibody reagent member, each antibody reagent member having a measurable or observable moiety labeled or chemically bonded thereto, wherein the antibody reagent member of said first antibody pair is said first antibody that specifically binds cardiac Troponin-I and the antibody reagent member of said second antibody pair is said second antibody that specifically binds N-terminal BNP,*

*such that the cardiac marker of cell injury and the marker of organ adaptation present in the sample will migrate toward the control region, bind to a cognate antibody pair to form an immobilized immunocomplex, and produce a color change proportional to the concentration of each marker in the sample, and*

*(b) visualizing or measuring the moiety labeled or chemically bonded to said first antibody and said second antibody so as to detect the presence of each marker in said sample.*

*14. The method of claim 10, wherein said first antibody is a monoclonal antibody and said second antibody is a monoclonal antibody.*

*15. The method of claim 10, wherein said first antibody is a polyclonal antibody and said second antibody is a polyclonal antibody.*

*16. The method of claim 6, wherein said increased levels are two-fold greater than in the control samples.*

*17. The method of claim 6, wherein steps (B) and (C) are carried out simultaneously.*

*18. The method of claim 10, wherein said increased levels are two-fold greater than in the control samples.*

*19. The method of claim 10, wherein steps (B) and (C) are carried out simultaneously.*

*20. The method of claim 10, wherein said first antibody is a monoclonal antibody and said second antibody is a polyclonal antibody.*

*21. The method of claim 10, wherein said first antibody is a polyclonal antibody and said second antibody is a monoclonal antibody.*

*22. The method of claim 6, wherein said first antibody specifically binds to cardiac Troponin-I; and said second antibody specifically binds to a N-terminal ANP.*

* * * * *